United States Patent [19]

Nordquist et al.

[11] Patent Number: 5,520,631

[45] Date of Patent: May 28, 1996

[54] METHOD AND APPARATUS FOR LOWERING THE INTRAOCULAR PRESSURE OF AN EYE

[75] Inventors: Robert E. Nordquist, Oklahoma City; Bing Li, Edmond, both of Okla.

[73] Assignee: Wound Healing of Oklahoma, Oklahoma City, Okla.

[21] Appl. No.: 279,506

[22] Filed: Jul. 22, 1994

[51] Int. Cl.$^6$ ................................................. A61M 5/00
[52] U.S. Cl. ................................................. 604/8; 623/4
[58] Field of Search .................... 623/4; 604/8–10, 604/289, 294

[56] References Cited

U.S. PATENT DOCUMENTS

| | | | |
|---|---|---|---|
| 3,915,172 | 10/1975 | Wichterle et al. . | |
| 4,060,081 | 11/1977 | Yannas et al. | 623/2 X |
| 4,457,757 | 7/1984 | Molteno | 604/294 |
| 4,501,263 | 2/1985 | Harbuck . | |
| 4,521,210 | 6/1985 | Wong | 604/8 |
| 4,554,918 | 11/1985 | White | 604/10 |
| 4,722,724 | 2/1988 | Schocket | 604/8 |
| 4,729,761 | 3/1988 | White | 604/8 |
| 4,750,901 | 6/1988 | Molteno | 604/8 |
| 4,787,885 | 11/1988 | Binder | 604/8 |
| 4,826,478 | 5/1989 | Schocket | 604/8 |
| 4,853,375 | 8/1989 | Krupin et al. | 514/152 |
| 4,886,488 | 12/1989 | White | 604/9 |
| 4,936,825 | 6/1990 | Ungerleider | 604/8 |
| 4,946,436 | 8/1990 | Smith | 604/8 |
| 4,968,296 | 11/1990 | Ritch et al. | 604/8 |
| 5,041,081 | 8/1991 | Odrich | 604/9 |
| 5,073,163 | 12/1991 | Lippman | 604/9 |
| 5,085,629 | 2/1992 | Goldberg et al. | 604/8 |
| 5,127,901 | 7/1992 | Odrich | 604/9 |
| 5,171,213 | 12/1992 | Price, Jr. | 604/9 |
| 5,178,604 | 1/1993 | Baerveldt et al. | 604/8 |
| 5,338,291 | 8/1994 | Speckman et al. | 604/9 |
| 5,370,607 | 12/1994 | Memmen | 604/8 |
| 5,391,201 | 2/1995 | Barrett et al. | 623/5 |
| 5,395,356 | 3/1995 | King et al. | 606/4 |
| 5,397,300 | 3/1995 | Baerveldt et al. | 604/8 |
| 5,401,508 | 3/1995 | Manesis | 623/5 X |
| 5,401,509 | 3/1995 | Robertson et al. . | |
| 5,401,510 | 3/1995 | Robertson et al. . | |

*Primary Examiner*—Mary Beth Jones
*Attorney, Agent, or Firm*—Head, Johnson & Kachigian

[57] ABSTRACT

A method and apparatus for lowering the intraocular pressure of an eye is disclosed and claimed. In the method of the invention, an opening is created in the limbus corneae region of the eye. A filtering implant having a foot portion and a body portion is provided for implantation. The foot portion of the implant is placed through the limbal opening into the anterior chamber of the eye, and the body portion is buried beneath a scleral flap. The apparatus of the invention is a filtering implant comprising a cellulosic membrane adapted to extend from the anterior chamber of the eye to a drainage area. Besides its draining function, the apparatus inhibits wound healing by occupying the space of the limbal opening. In its preferred embodiment, the implant comprises a goblet-shaped glucose homopolymer membrane having foot, neck and body portions. The foot portion of the membrane is of a general rectangular shape, while the body portion is bell-shaped. The neck segment connects the foot portion to the body portion.

10 Claims, 2 Drawing Sheets

METHOD AND APPARATUS FOR LOWERING THE INTRAOCULAR PRESSURE OF AN EYE

BACKGROUND OF THE INVENTION

1. Technical Field

This invention relates to ophthalmic implants and the manipulation of the intraocular pressure of the eye, and, more particularly, to a new and useful method and apparatus for lowering intraocular pressure by draining aqueous humor from the anterior chamber of the eye and by mechanically inhibiting wound healing at the surgical site.

2. Background

Glaucoma is a disorder characterized by increased intraocular pressure. It may cause impaired vision, ranging from slight sight loss to absolute blindness as a result of glaucomatous optic neuropathy. The causes of glaucoma are poorly understood; however, vasomotor and emotional instability, hyperopia, and especially heredity are among the predisposing factors. The increased intraocular pressure incident to glaucoma is related to an imbalance between production and outflow of aqueous humor, the watery fluid that fills the anterior and posterior chambers of the eye. Aqueous humor is secreted by the ciliary processes of the eye, and passes through the posterior chamber and the pupil into the anterior chamber where it is reabsorbed into the venous system at the iridocorneal angle by way of the sinus venosus, also called the canal of Schlemm. Obstruction of aqueous humor outflow appears to be mainly responsible for elevated intraocular pressures.

Glaucoma is a significant healthcare problem with immediate and long term ramifications, both physical and financial. Glaucoma is responsible for approximately ten percent of all blindness worldwide and is the leading cause of blindness in the United States, where over 300,000 new cases are reported each year. In the U.S., more than 95,000 glaucoma patients lose some degree of sight each year due to the disease, with greater than 5,500 experiencing total blindness. As treatment costs on a per year basis are estimated to be $1.5 billion, based upon more than two million annual office visits, the socio-economic impact of glaucoma is significant.

Along with persons predisposed to glaucoma by virtue of family history, individuals at higher risk of developing glaucoma are those 35 years of age or older or those with diabetes or positive glucose tolerance tests. The disease also strikes African-Americans in disproportionate numbers. They are four to five times more likely to develop glaucoma and are up to six times more apt to suffer a complete loss of sight.

The aim of current glaucoma treatment is the prevention of optic nerve damage and vision loss by lowering intraocular pressure. Common treatments for glaucoma include the systemic use of carbonic anhydrase inhibitors or topical applications of pilocarpine, timolol maleate, betaxolol HCl, levobunolol, metipranolol, epinephrine, dipivefrin, demecarium bromide, and echothiophate iodide. But, as is the case with most significant chemical therapies, the side effects of these medications may be severe while the treatment's efficacy is variable. When medication fails to control intraocular pressure, or visual fields show progressive defects, various glaucoma operations have been used to improve aqueous humor drainage. It has been reported that in 1993 over 1,152,000 operations for regulating intraocular pressure were performed in the U.S. alone.

While laser trabeculoplasty (alteration of the trabecular meshwork) has been utilized to a limited extent to improve aqueous drainage, glaucoma filtration surgery is the most widely practiced procedure when dealing with severe glaucoma cases. The fundamental principle of this surgery is to create an opening, or fistula, at the limbal region of the eye to facilitate the drainage of the aqueous humor, bypassing the pathological blockage in the anterior chamber angle. There are two basic approaches currently in use. In a full-thickness filtration procedure, a full-thickness sclerostomy is made, connecting the anterior chamber directly to the subconjunctival space. The main advantage of this procedure is the significantly lower intraocular pressures achieved postoperatively. However, because of its complications, this surgery is less frequently used than the second type of surgery, the trabeculectomy. In the trabeculectomy, a sclerostomy is performed under a scleral flap. This flap is then sutured back to its original bed in an attempt to minimize aqueous outflow runoff. The advantage of the trabeculectomy under the scleral flap is the tamponate effect provided by the resutured sclera causing a subsequent reduction of aqueous flow-through. Unfortunately, although this procedure provides short-term postoperative stability, final intraocular pressure levels are usually higher than those seen after full-thickness filtration, and the long term success rate is lower.

A problem with both these procedures, and glaucoma filtration surgery in general, is the body's natural healing process. Glaucoma filtration surgery differs from most surgical procedures in that inhibition of wound healing is desirable to achieve surgical success. When normal wound healing occurs, filtration rates decrease and intraocular pressures rise, making necessary the inhibition of the healing response. Surgical failures occur most frequently due to an overwhelming wound healing response and scarring of the filtering site. Histological studies of human and lab animal surgeries suggest that failure of glaucoma filtration surgery is associated with the presence of dense fibrovascular connective tissue around the surgical site. This prevents diffusion of the aqueous humor from the subconjunctival space.

To defeat the healing process, aqueous shunts have become an increasingly popular and effective means of lowering intraocular pressure. Among the various devices heretofore used, translimbal equatorial shunts have proven most effective. Examples of such devices include those disclosed in United States patents granted to Molteno (U.S. Pat. Nos. 4,457,757 and 4,750,901), Odrich (U.S. Pat. Nos. 5,041,081 and 5,127.901), and Baerveldt et al. (U.S. Pat. No. 5,178,604). Molteno's devices generally consist of ridged plates having drainage tubes for insertion into the anterior chamber of the eye. Odrich's patents disclose two ophthalmic implants for relieving pressure in the anterior chamber, both having one-way flow resisting valves, and residing under the conjunctiva. Baerveldt's apparatus comprises an elastomeric plate having a drainage tube tunneled through Tenon's capsule and the cornea and inserted into the anterior chamber.

The major disadvantage of current aqueous drainage devices is excessive aqueous drainage in the immediate postoperative period resulting in a flat anterior chamber and potential choroidal detachment. Profound hypotony, possibly leading to phthisis bulbi, is also a substantial risk. Excessive postoperative aqueous flow also causes expansion of the fibrous capsule beneath the rectus muscles of the eye. This mass effect stretches and tightens the muscles inducing heterotropia and motility restriction into the quadrant of the implant. A mass effect also may be exerted simply by the bulky presence of the device itself beneath the muscle causing scleral erosion, changes in eye curvature, or damage to adjacent vasculature and tissue. This is particularly true of rigid plastic or metal implants. Further problems with glaucoma filtration surgery include the conventional need for peripherial iridotomies, wherein a transverse division of some of the fibers of the iris is performed to create a communication between the anterior chamber and the posterior chamber. Other problems involve friction and wear imparted to the scleral flap by implanted devices, irritation of the iris endothelium caused by placement of implants into the anterior chamber, and aggravation produced by chronic forward and backward movement of the implants. In spite of these shortcomings, aqueous drainage devices have been successful in many cases, but the operative procedure remains challenging and significant complications are not unusual.

SUMMARY OF THE INVENTION

It is thus an object of the present invention to provide a method and apparatus for lowering the intraocular pressure of an eye which control aqueous drainage in the immediate postoperative period such that there is no excessive flattening of the anterior chamber and, consequently, no choroidal detachment.

It is an additional object of the invention to furnish a method and apparatus for lowering intraocular pressure which regulate the degree of aqueous drainage over the long term, reducing the instance of profound hypotony and phthisis bulbi normally encountered in connection with other glaucoma filtration surgeries.

It is a further object of the invention to supply a method and apparatus for lowering intraocular pressure which control aqueous drainage while preventing excessive expansion of the fibrous capsule beneath the rectus muscles of the eye and concomitant heterotropia and motility restriction.

Another object of the invention is to provide a method and apparatus for lowering intraocular pressure which abolish the need for a peripheral iridotomy, thereby reducing the risk of vitreous damage.

Yet another object of the invention is to furnish a method for surgically implanting an intraocular filtration device, which procedure is relatively simple and has few complications.

A still further object of the invention is to provide an implant for lowering intraocular pressure which is small and slender and whose construction mechanically inhibits wound healing at the surgical site and lessens the likelihood of scleral erosion, changes in eye curvature, or damage to adjacent vasculature and tissue. It is also an object of the invention that the construction of the provided implant solves problems of friction and wear imparted to a scleral flap, irritation of the iris endothelium, and aggravation produced by implant movement.

These and other objects and advantages are achieved by the method and apparatus disclosed and claimed herein. In the method of the invention, an opening is created in the limbus corneae region of the eye. A filtering implant having a foot portion and a bowl or body portion is provided for implantation. The foot portion of the implant is placed through the limbal opening into the anterior chamber of the eye, and the body portion is buried beneath a scleral flap. The preferred embodiment of the method invention includes cutting or stamping out the goblet shaped form, then thoroughly rinsing it in distilled water. The cellulosic membrane device is then heated to 100° C. for 30 minutes in a solution of 2% sodium bicarbonate and 1% ethylenediaminetetraacetic acid, followed by cooling at 4° C. in balanced saline solution. After rinsing again in a balanced saline solution the formed device may be placed in a container of a solution of sterile de-ionized water and sterilized by autoclave for storage until use at another time. A trabeculectomy is performed to obtain a limbal opening, and the foot portion of the goblet-shaped cellulosic membrane is inserted into the anterior chamber of the eye such that the foot portion is positioned at a point anterior of the trabecular meshwork. (The trabecular meshwork, also known as the reticulum trabeculare, refers to the network of fibers at the iridocorneal angle between the anterior chamber of the eye and the venous sinus of the sclera.) The bowl, or bell-shaped, portion of the membrane is then buried in an episcleral space beneath a layer of vascularized tissue.

The apparatus of the invention is a filtering implant comprising a cellulosic membrane adapted to extend from the anterior chamber of the eye to a drainage area. In its preferred embodiment, the implant comprises a goblet-shaped glucose homopolymer membrane having foot, neck and body portions. The foot portion of the membrane is of a general rectangular shape, while the body portion is bell-shaped. The neck segment connects the foot portion to the body portion. The membrane is of a minimal thickness in the range of 0.15 mm. While the dimensions of the implant may be altered to take into account individual patient variables, the standard implant measures 1 mm×6 mm in the foot portion, 2 mm×2.5 mm in the neck, and 10 mm×6 mm in the body section. The implant is also provided with a center cut line extending through the foot and neck regions.

DETAILED DESCRIPTION OF THE PREFERRED EMBODIMENT

Figure 1:
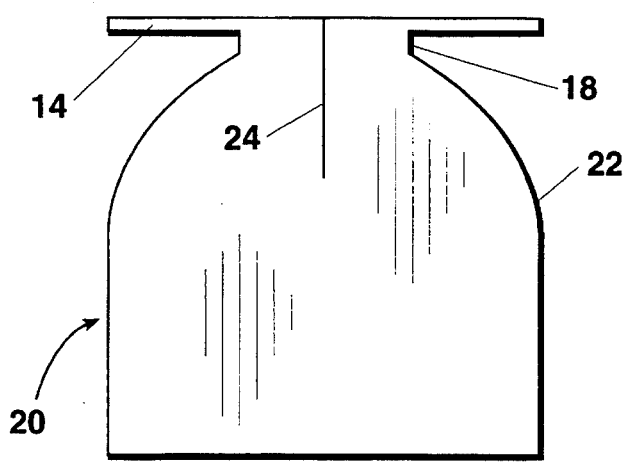
FIG. 1 is a front elevational view of the preferred embodiment of the apparatus of the invention.
Figure 2:
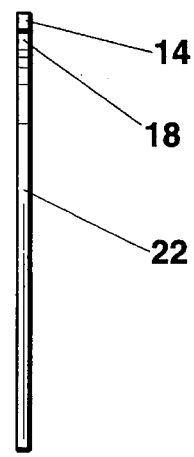
FIG. 2 is a side elevational view of the preferred embodiment of the apparatus of the invention.

Referring to FIG. 1 and 2, the implant 20 of the present invention is goblet-shaped in two dimensions (as shown in FIG. 1) and is relatively flat in the third (FIG. 2). Overall, implant 20 may be alternately described as being of a generally rectangular shape having three altered margins—a central cut line and two side notches. The altered margins result in implant 20 being composed of three segments or portions. A foot portion 14 is generally rectangular in shape. A body portion, or bowl, 22 is of a bell shape. A neck region 18 connects foot portion 14 to body portion 22, neck region 18 being of a smaller width than both foot portion 14 and body portion 22. A center cut line 24 runs from the center of foot portion 14 through neck region 18 part way into body portion 22. In other words, implant 20 is center cut through foot portion 14 and neck region 18.

Before discussing the preferred dimensions of implant 20, it should be understood that the dimensions are alterable to the extent necessitated by individual patient variables such as the size of the eye, amount of pressure in the eye, and the age of the patient. Usual dimensions, however, include foot portion 14 measuring approximately 1 mm×6 mm. Neck portion 18 is about 2 mm×2.5–3 mm, while body portion 22 measures approximately 10 mm×6 mm. Implant 20 is relatively flat as shown in FIG. 2, with a preferred thickness of around 0.15 mm.

Implant 20 is made from a cellulosic membrane. The cellulosic membrane is a naturally occurring compound which consists of a homopolymer of glucose units connected in a 1,4'βlinkage. In nature, cellulose exists as a series of extremely high molecular weight polymers which associate together in an ordered state. Native cellulose is extraordinarily insoluble in water as well as most organic solvents. Until now, the principal applications of cellulosic membranes have been in the areas of pharmacology, clinical and biological chemistry, and food chemistry. Cellulosic membranes have shown themselves especially useful in the field of dialysis.

That implant 20 is composed of a cellulosic material is significant. This makes implant 20 soft enough to avoid eye tissue damage, flaccid enough to be easily seated in a surgical bed and to conform to the curvature of the surgical site, and strong enough to keep the surgical fistula open permanently. Additionally, because of its composition, implant 20 is easy to size and modify such that the extrinsic ocular motility is not disturbed subsequent to the implant procedure. Further, the surface of implant 20 as constructed from the cellulosic material is so smooth as to resist cellular attachment and invasion. Implant 20 is also nonabsorbable and stable at body temperature.

Figure 3:
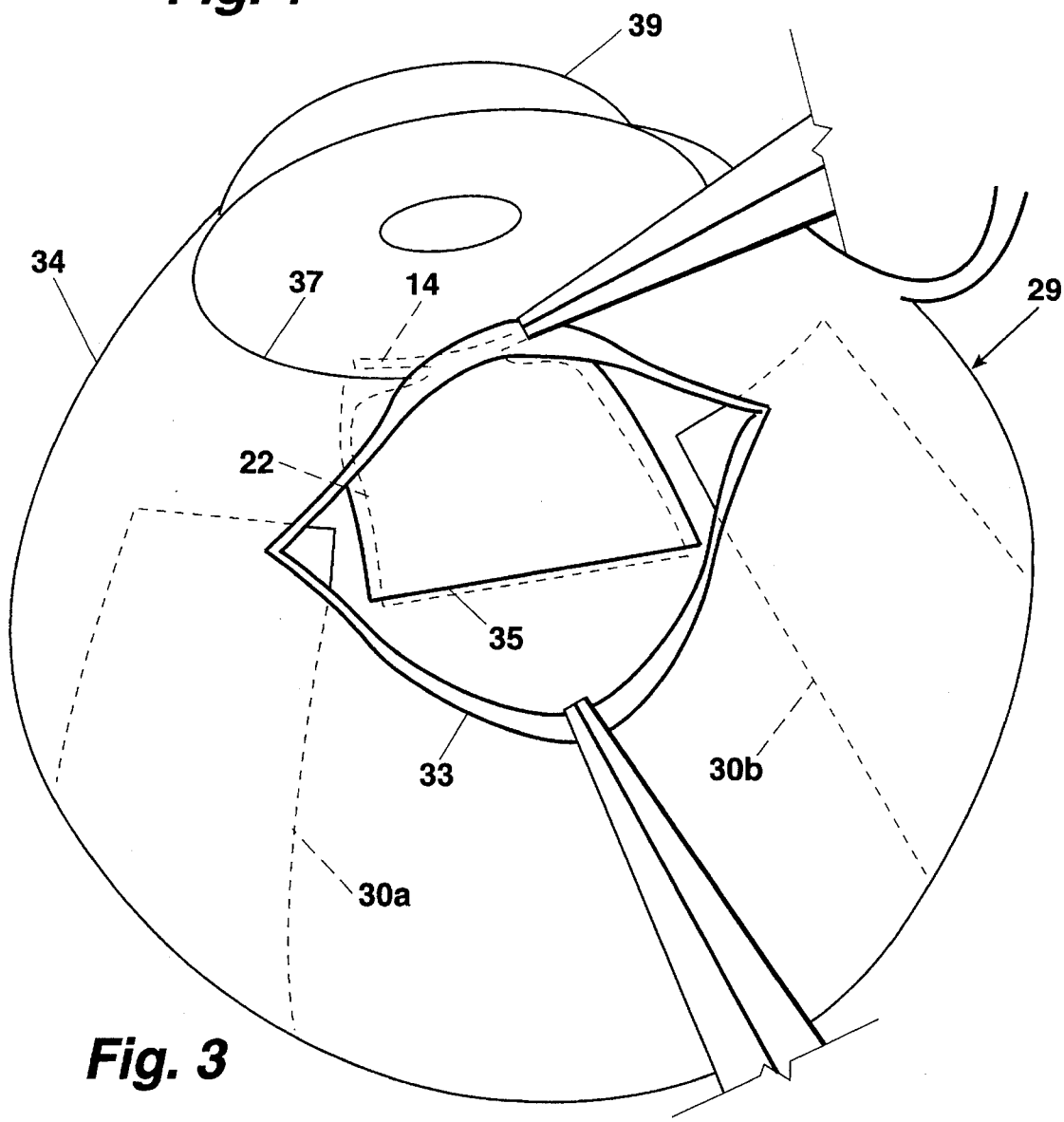
FIG. 3 is a perspective view of the preferred embodiment of the apparatus as implanted into an eye in accordance with the method of the invention.
Figure 4:
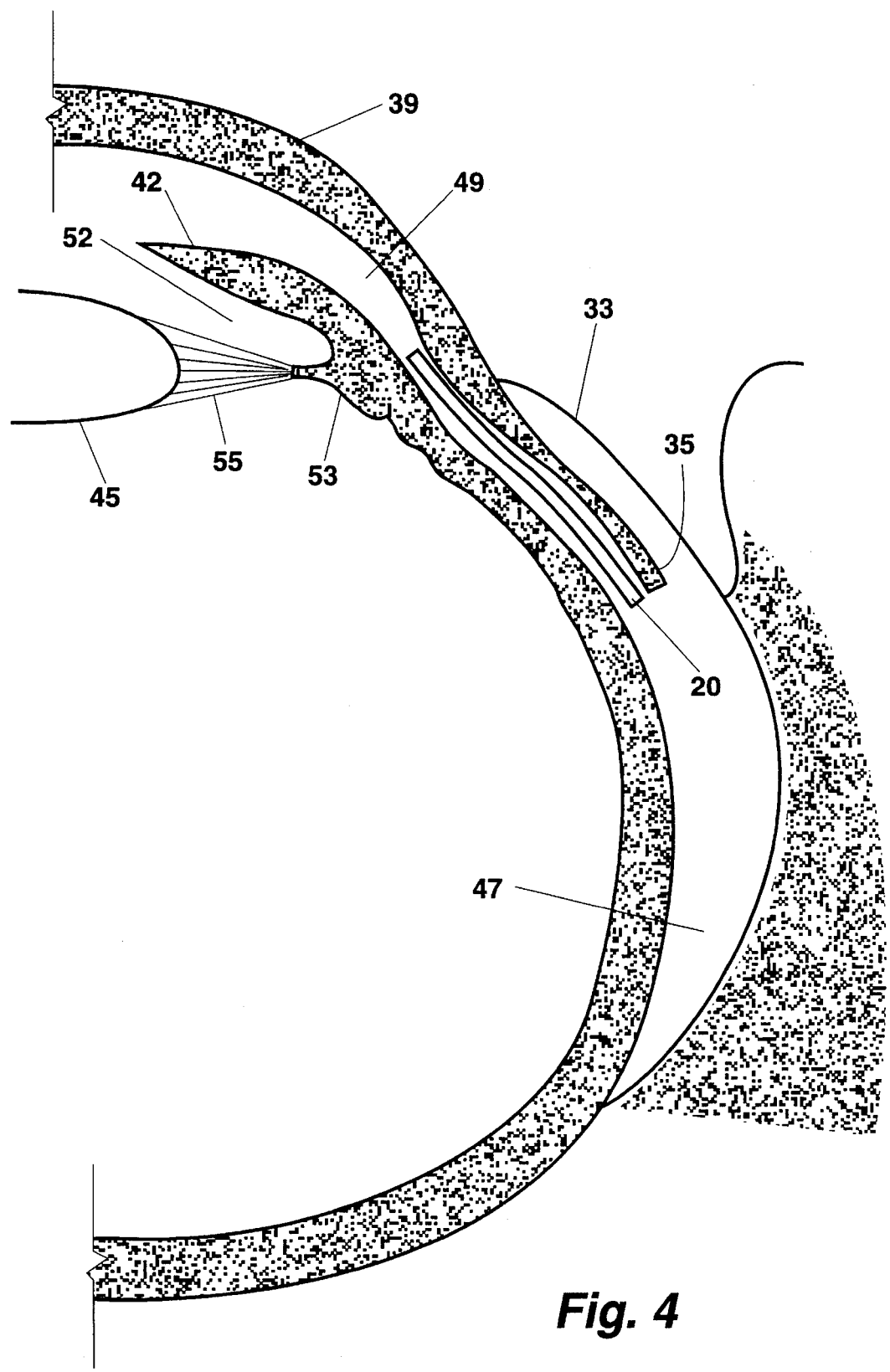
FIG. 4 is a cross-sectional view of the preferred embodiment of the apparatus after implantation into an eye in accordance with the method of the invention.

Turning now to FIG. 3, where eye 29 is shown in a perspective view taken during a surgical filtration procedure, and to FIG. 4 which shows a cross-section of eye 29 after the performance of a filtration procedure, sclera 34 and cornea 39 form the external tunic of the eyeball. They are essentially fibrous in structure, sclera 34 being opaque and forming the posterior five-sixths of the globe, and cornea 39 being transparent and forming the remaining one-sixth. Sclera 34 serves to maintain the form of the globe of eye 29 while cornea 39 facilitates the transmission of light to the inner eye and protects, as a cover, the structures of the inner eye. The external surface of sclera 34 is of a white color and is quite smooth, except at the insertion points of rectus muscles 30a–b. The anterior part of sclera 34 is covered by the conjunctival membrane 33, also called the conjunctiva. Conjunctiva 33 is the mucous membrane of the eye. It lines the inner surface of the eyelids, where it is thick, opaque, and highly vascular, and is reflected over the fore part of sclera 34 and cornea 39. Upon sclera 34, conjunctiva 33 is loosely connected to the globe of eye 29 where it has become thinner, transparent, and only slightly vascular. Upon cornea 39, conjunctiva 33 consists only of epithelium, constituting the anterior layer of the cornea, known as the corneal epithelium. The sclerocorneal junction is known as the limbus corneae 37. This is where the margin of cornea 39 is overlapped by sclera 34. The anterior chamber 49 is the space bounded in front by cornea 39 and behind by the iris 42. The posterior chamber 52 is a narrow chink between the peripheral part of iris 42, the suspensory ligament 55 of the lens 45 and the ciliary processes 53. The aqueous humor completely fills both anterior chamber 49 and posterior chamber 52. The aqueous humor is little more than water in composition, as less than one-fiftieth of its weight is solid matter, that being chiefly sodium chloride.

In the preferred embodiment of the method of the invention, conjunctiva 33 is opened such that sclera 34 and limbus corneae 37 are accessible. A section of sclera 34 is excised to obtain scleral flap 35, and a limbal opening is made into anterior chamber 49. Implant 20 is folded along center cut line 24 so that foot segment 14 is easily insertable through the limbal opening into the iridocorneal angle of anterior chamber 49. Body portion 22 is set into the surgical bed beneath scleral flap 35, after which scleral flap 35 is sutured closed. The body portion 22 is preferably buried to depth between 50% and 70% of the scleral thickness. Conjunctiva 33 is likewise sutured shut. A filter bleb 47 is formed in a space under conjunctiva 33 as a result of the implantation of implant 20. Though it is solid, implant 20 diffuses water such that the aqueous humor of anterior chamber 49 passes through implant 20 into filter bleb 47 to be disseminated in sclera 34 and absorbed by the body. A small amount of aqueous humor may also pass through conjunctiva 33. Similar to a dialysis membrane, implant 20 functions to allow the passing of fluids without permitting the leaching of proteins or other particulates from the aqueous humor.

The proposed glaucoma filtration procedure was performed utilizing the implant of the present invention in six rabbits in a preliminary trial. The foot of the goblet-shaped implant was passed into the anterior chamber of the eye through a limbal opening and the body portion was buried beneath a scleral flap. This new procedure significantly lowered the intraocular pressure in all experimental rabbit eyes as shown in Table 1 below.

TABLE 1

| | | IOP difference (experimental/control) average over study period | | | | |
|---|---|---|---|---|---|---|
| Rabbit | | Baseline | Post-op Day 1–3 | Post-op Day 4–7 | Post-op Day 8–15 | Post-op Day 16–30 | Post-op Day 31–70 |
| 1. | Exper. | 18.7 ± 0.5 | 11.3 ± 1.7 | 12.3 ± 1.3 | 17.6 ± 1.8 | 13.1 ± 4.6 | 13.0 ± 4.4 |
| | Control | 19.7 ± 1.2 | 10.3 ± 3.0 | 23.3 ± 1.0 | 22.8 ± 4.3 | 19.1 ± 2.8 | 19.9 ± 3.64 |
| 2. | Exper. | 20.0 ± 0 | 12.3 ± 1.9 | 12.0 ± 0 | 15.25 ± 1.0 | 16.9 ± 2.4 | 16.0 ± 2.7 |
| | Control | 25.3 ± 0.5 | 27.3 ± 3.3 | 22.5 ± 1.8 | 22.1 ± 1.5 | 20.6 ± 1.7 | 21.1 ± 2.5 |
| 3. | Exper. | 22.7 ± 0.5 | 18.0 ± .08 | 13.1 ± 0.9 | 14.25 ± 1.4 | 14.8 ± 3.3 | 15.0 ± 2.91 |
| | Control | 21.0 ± 0 | 18.7 ± 0.5 | 17.5 ± 2.1 | 17.8 ± 1.8 | 18.1 ± 2.5 | 18.7 ± 2.6 |
| 4. | Exper. | 23.0 ± 0.5 | 16.0 ± 1.4 | 16.0 ± 0.7 | 16.9 ± 0.9 | 16.1 ± 1.4 | 16.0 ± 1.2 |
| | Control | 23.0 ± 0 | 12.0 ± 2.9 | 17.5 ± 3.8 | 23.0 ± 6.7 | 23.5 ± 4.2 | 22.4 ± 4.9 |
| 5. | Exper. | 24.7 ± 0.5 | 16.3 ± 1.7 | 13.0 ± 1.2 | 15.8 ± 2.6 | 16.0 ± 1.4 | 14.0 ± 3.1 |
| | Control | 24.7 ± 0.5 | 14.3 ± 2.0 | 17.5 ± 3.2 | 21.4 ± 4.4 | 21.5 ± 2.2 | 20.1 ± 3.6 |
| 6. | Exper. | 22.7 ± 0.5 | 14.7 ± 0.5 | 12.5 ± 1.1 | 13.0 ± 2.7 | 14.4 ± 1.8 | 12.0 ± 3.07 |
| | Control | 22.7 ± 0.5 | 14.7 ± 2.5 | 16.3 ± 2.8 | 16.5 ± 4.1 | 17.6 ± 2.6 | 18.8 ± 4.43 |

In accordance with the protocol of the trial, a cellulosic membrane source was rinsed thoroughly in distilled water, heated to 100° C. for 30 minutes in 2% sodium bicarbonate and 1% ethylenediaminetetraacetic acid solution, then cooled and stored at 4° C. in 2% formaldehyde. The treated cellulosic membrane was rinsed twice in a balanced saline solution and then was cut into goblet-shaped forms (see FIG. 1). The devices were placed in one eye of New Zealand White rabbits while the other eye served as a control with glaucoma filtering surgery only. The foot portion was placed in the anterior chamber. The neck segment was passed through a hole in the limbus that was created by excision of a 2 mm×1 mm×0.5 mm section of the scleral wall at the 1:00 o'clock position. The bowl portion of the device was placed in the surgical bed under the scleral flap. The scleral flap was sutured with one or two 8/0 chromic collagen sutures. The conjunctiva was closed using 6/0 nylon or silk sutures. Peripheral iridotomies were not needed. The surgical procedure typically lasted 20 to 30 minutes, and several refinements were made in the course of the study. The foot of the device was buried deep in the angle of the anterior chamber in all the rabbits except Rabbit No. 1. The foot of the device in Rabbit No. 1 was positioned just inside the angle but did not project into the anterior chamber. The intraocular pressures of the eyes of each animal, as measured by pneumotonometry under topical anesthesia, were recorded daily at the same hour. Two investigators independently measured pressures and then averaged the two values. The pressures in the experimental eyes and control eyes were recorded for each animal. Baseline intraocular pressures of the rabbits were measured for three days prior to implant. The rabbits were euthanized at the end of the study and the globes enucleated. The globes were fixed in formaldehyde, processed routinely, and stained with hematoxylin and eosin.

During the 70 day study period, the surgery was followed by direct observation for bleb formation, for surgical effect on the cornea and anterior chamber, and for measurement of intraocular pressure. None of the rabbits developed corneal decompensation, conjunctival erosion or uveitis as a result of the implant. One day postoperatively, the eyes exhibited a slight to moderate inflammation of the conjunctiva in the area of the implant. Within seven days, however, the inflammation of the conjunctiva gradually subsided. Immediately after surgery the anterior chambers were flat or normal. Within twenty-four hours normal anterior chambers were formed in all cases. The anterior chamber humor was very clear at three days postoperatively in all rabbits.

The differences between the intraocular pressure of the experimental eye and of the control eye for each of six rabbits over 70 days are shown in Table 1. In the experimental eye group, the daily intraocular pressures were significantly lower than those for the control eye ($P<0.05$). Only four percent of the daily experimental eye pressure measurements were greater than 19 mmHg while seventy percent of the control eye measurements were greater. Eighty percent of daily experimental eye pressure measurements were between 12–16 mmHg, while in contrast only four percent of the control eye measurements fell within this range. All control eye blebs failed within 14 days, while five of six experimental eyes still maintained a functional filtering bleb at the end of the experiment. The globes were examined by light microscopy. These observations showed that the foot had entered the anterior chamber anterior to the trabecular meshwork. There was no evidence of corneal endothelial damage in any of the globes. Further posteriorly, the bowl lay within the sclera at a depth of 50 to 60 percent. There was iris touch of the foot in all six experimental eyes, but no necrosis, atrophy or hypertrophy was found.

Many advantages are obtained through the use of the method and apparatus of the present invention. As the implant is designed to permit the regulated flow of fluids through it, aqueous drainage is achieved in a consistent and predictable fashion. Additionally, the placement of the neck of the device in the limbal opening virtually eliminates closure by both immediate and chronic tissue responses. Further, the need for a peripherial iridotomy is abolished, thereby reducing the risk of vitreous damage.

More advantages are gained by the composition of, and shape of, the implant. As the implant is constructed of a cellulosic membrane, it is easy to form and may be pre-manufactured to varying dimensions at a low cost. It is also non-toxic to eye tissue and can be sterilized by boiling or autoclave. The flat profile and flaccid nature of the device work to reduce friction and wear on the scleral flap and promote the conformation of the device to the natural curvature of the eye without imparting a mechanical resistance which could produce scleral erosion or a change in eye curvature. Also owing to the shape of the device, the small neck functions to form a fistula and the body or bowl of the implant forms the filtration area. Because the foot portion of the implant sets in the anterior chamber, it works to keep the entrance to the fistula open. Additionally, as the body and foot are considerably wider than the neck, the implant is inhibited from forward or backward displacement. The shape of the device also makes implantation possible without the need for sutures to hold the device in place. Still further, because the implant is center cut, the necessary size of the limbal opening is reduced. This feature also helps to lessen the occurrence of post surgical hypotony and the chance of iris endothelium irritation upon insertion of the foot of the implant into the anterior chamber.

While the invention has been described with a certain degree of particularity, it is manifest that many changes may be made in the details of construction and the arrangement of components without departing from the spirit and scope of this disclosure. It is understood that the invention is not limited to the embodiment set forth herein for purposes of exemplification, but is to be limited only by the scope of the attached claim or claims, including the full range of equivalency to which each element thereof is entitled.

What is claimed is:

1. A method for lowering the intraocular pressure of an eye, which comprises:
   (a) creating an opening in the limbus corneae that is about 2.5 mm–3 mm wide to provide access to the anterior chamber of said eye;
   (b) providing a filtering implant, said implant being generally rectangular in shape and having two side notches defining a foot portion and a body portion, said foot portion measuring approximately 1 mm (length)×6 mm (width);
   (c) placing said foot portion through said opening into said anterior chamber; and
   (d) completely burying said body portion in a surgical bed beneath a scleral flap to a depth between 50 and 70 percent of the scleral thickness.

2. The method according to claim 1, wherein said foot is placed into said anterior chamber at a point anterior to the trabecular meshwork.

3. The method according to claim 1, wherein said implant is center cut through said foot portion.

4. The method according to claim 1, wherein said opening is created by excising a section of the scleral wall at the 1:00 o'clock position.

5. The method according to claim 1, wherein said implant comprises a cellulosic membrane.

6. A method for lowering the intraocular pressure of an eye, which comprises:

(a) thoroughly rinsing a cellulosic membrane in distilled water;

(b) heating said cellulosic membrane to 100° C. for 30 minutes in 2% sodium bicarbonate and 1% ethylenediaminetetraacetic acid;

(c) cooling said cellulosic membrane at 4° C. in 2% formaldehyde or balanced saline solution;

(d) rinsing said cellulosic membrane in a balanced saline solution;

(e) cutting said cellulosic membrane into a generally rectangular shape having altered margins so as to form a foot portion and a body portion;

(f) creating an opening in the limbus corneae;

(g) placing said foot portion through said opening into the anterior chamber of said eye; and (h) burying said body portion beneath a scleral flap.

7. The method according to claim 6, wherein said opening is about 2.5 mm–3 mm wide.

8. The method according to claim 6, wherein said foot portion measures approximately 1 mm (length)×6 mm (width).

9. The method according to claim 6, wherein said implant has a thickness of approximately 0.15 mm.

10. The method according to claim 6, wherein said implant is buried to a depth between 50 and 70 percent of the scleral thickness.

\* \* \* \* \*